United States Patent
Hoshishima (10) Patent No.: US 9,052,288 B2
(45) Date of Patent: Jun. 9, 2015

(54) FLUORESCENCE MEASURING APPARATUS AND FLUORESCENCE MEASURING METHOD

(75) Inventor: Kazuteru Hoshishima, Tamano (JP)

(73) Assignee: MITSUI ENGINEERING & SHIPBUILDING CO., LTD., Tokyo (JP)

( * ) Notice: Subject to any disclaimer, the term of this patent is extended or adjusted under 35 U.S.C. 154(b) by 448 days.

(21) Appl. No.: 13/575,107

(22) PCT Filed: Jan. 13, 2011

(86) PCT No.: PCT/JP2011/000116
§ 371 (c)(1),
(2), (4) Date: Jul. 25, 2012

(87) PCT Pub. No.: WO2011/089866
PCT Pub. Date: Jul. 28, 2011

(65) Prior Publication Data
US 2012/0286171 A1   Nov. 15, 2012

(30) Foreign Application Priority Data

Jan. 25, 2010   (JP) ................ 2010-012898

(51) Int. Cl.
*G01N 21/64* (2006.01)
*G01N 15/14* (2006.01)
*G01N 15/00* (2006.01)

(52) U.S. Cl.
CPC ........ *G01N 21/6408* (2013.01); *G01N 15/1459* (2013.01); *G01N 2015/0038* (2013.01)

(58) Field of Classification Search
CPC .......... G01N 2021/6428; G01N 21/64; G01N 21/6408
USPC ...................................... 250/458.1
See application file for complete search history.

(56) References Cited

U.S. PATENT DOCUMENTS

2003/0099574 A1   5/2003   Bentsen et al.
2004/0101851 A1   5/2004   White et al.
(Continued)

FOREIGN PATENT DOCUMENTS

JP   2002-102147 A   4/2002
JP   2005-501256 A   1/2005
(Continued)

OTHER PUBLICATIONS

International Search Report of corresponding International Application No. PCT/JP2011/000116, dated on Apr. 5, 2011.
(Continued)

*Primary Examiner* — Casey Bryant
(74) *Attorney, Agent, or Firm* — Global IP Counselors, LLP (57) ABSTRACT

Disclosed herein is a fluorescence measuring apparatus capable of determining whether accuracy of measuring fluorescence lifetime is deteriorated or not due to adjustment of the apparatus. The fluorescence measuring apparatus for measuring fluorescence emitted when an objects to be measured are irradiated with laser light includes: a laser light source that irradiates each of the objects to be measured with intensity-modulated laser light; a light-receiving unit that receives fluorescence emitted when each of the objects to be measured is irradiated with the laser light; a signal processing unit that determines a fluorescence lifetime using a signal of the fluorescence received by the light-receiving unit; and a determining unit that determines whether or not a fluorescence lifetime dispersion of the objects caused by amplification of the signal of the fluorescence performed by the light-receiving unit or by the signal processing unit is larger than a predetermined value.

12 Claims, 9 Drawing Sheets

(56) References Cited

U.S. PATENT DOCUMENTS

| | | |
|---|---|---|
| 2005/0239117 A1 | 10/2005 | Tanaami et al. |
| 2006/0049978 A1* | 3/2006 | Siegel .......................... 342/159 |
| 2009/0012721 A1* | 1/2009 | Kimura et al. ................. 702/23 |
| 2012/0181937 A1* | 7/2012 | Jaffe et al. ..................... 315/151 |

FOREIGN PATENT DOCUMENTS

| | | |
|---|---|---|
| JP | 2005-308504 A | 11/2005 |
| JP | 2006-507507 A | 3/2006 |
| JP | 2006-227013 A | 8/2006 |
| JP | 2007-101397 A | 4/2007 |
| JP | 2008-256380 A | 10/2008 |
| WO | WO-99/58955 A1 | 11/1999 |

OTHER PUBLICATIONS

Shigeyuki Nakada et al., "Development of Fluorescence Lifetime FRET Flow Cytometer", Mitsui Zosen Technical Review, Mar. 31, 2007, No. 190, pp. 54 to 60.

\* cited by examiner

FLUORESCENCE MEASURING APPARATUS AND FLUORESCENCE MEASURING METHOD

TECHNICAL FIELD

The present invention relates to an apparatus and a method for measuring fluorescence emitted when an object to be measured is irradiated with laser light.

BACKGROUND ART

A fluorescence measuring apparatus is known which acquires information about an object to be measured by irradiating the object to be measured with laser light and receiving fluorescence emitted from the object to be measured.

A flow cytometer using such a fluorescence measuring apparatus can acquire information per object to be measured by allowing objects to be measured such as cells, DNAs, RNAs, enzymes, or proteins labeled with a fluorochrome to flow in a sheath fluid, irradiating the objects to be measured with laser light, and measuring fluorescence emitted from the fluorochrome labeling the objects to be measured.

Further, another fluorescence measuring apparatus is known which acquires a fluorescence relaxation time constant by irradiating an object to be measured with laser light whose intensity is modulated at a predetermined frequency and receiving fluorescence emitted from the object to be measured (Patent Document 1).

CITATION LIST

Patent Document

Patent Document 1: JP-A-2007-101397

SUMMARY OF INVENTION

Technical Problem

Fluorescence received by a fluorescence measuring apparatus has a wide dynamic range, and therefore when receiving very weak fluorescence, the fluorescence measuring apparatus amplifies a signal of the fluorescence before signal processing. For this reason, when the fluorescence measuring apparatus determines a fluorescence lifetime from received fluorescence, a photomultiplier tube that converts the received fluorescence into an electric signal and an amplifier that amplifies the electric signal are used. When the gain of the photomultiplier tube or of the amplifier used in the fluorescence measuring apparatus is not proper, the accuracy of a fluorescence lifetime determined by the fluorescence measuring apparatus is deteriorated. Therefore, the gains of the photomultiplier tube and of the amplifier are preferably adjusted to proper values.

However, not all the users can easily determine whether or not the gains of the photomultiplier tube and of the amplifier are proper. Therefore, when it is difficult for a user to determine whether or not the gains of the photomultiplier tube and of the amplifier are proper, there is a possibility that the accuracy of a fluorescence lifetime determined by the fluorescence measuring apparatus is deteriorated.

It is therefore an object of the present invention to provide a fluorescence measuring apparatus and a fluorescence measuring method which are capable of determining whether accuracy of measuring fluorescence lifetime is deteriorated or not due to adjustment of the apparatus.

Solution to Problem

A fluorescence measuring apparatus of present invention is a fluorescence measuring apparatus for measuring fluorescence emitted when objects to be measured are irradiated with laser light, including: a laser light source that irradiates each of the object to be measured with intensity-modulated laser light; a light-receiving unit that receives fluorescence emitted when each of the object to be measured is irradiated with the laser light; a signal processing unit that determines a fluorescence lifetime using a signal of the fluorescence received by the light-receiving unit; and a determining unit that determines whether or not a fluorescence lifetime dispersion of the objects caused by amplification of the signal of the fluorescence performed by the light-receiving unit or by the signal processing unit is larger than a predetermined value.

Preferably, the light-receiving unit has a photomultiplier tube, and the signal processing unit has an amplifier that amplifies the signal of the fluorescence received by the light-receiving unit.

Preferably, the fluorescence measuring apparatus further includes a gain adjusting unit that adjusts a gain of the photomultiplier tube or of the amplifier based on a result of determination made by the determining unit.

Preferably, the fluorescence measuring apparatus further includes an output unit that outputs a result of determination made by the determining unit.

Preferably, the output unit outputs a magnitude of the fluorescence lifetime dispersion.

Preferably, the signal processing unit determines the fluorescence lifetime based on a phase difference between a modulation signal for modulating an intensity of the laser light and the signal of the fluorescence received by the light-receiving unit.

A fluorescence measuring method of present invention is a fluorescence measuring method for measuring fluorescence emitted when objects to be measured are irradiated with laser light, the method including: irradiating each of the object to be measured with intensity-modulated laser light; receiving fluorescence emitted when each of the object to be measured is irradiated with the laser light; performing signal processing to determine a fluorescence lifetime using a signal of the fluorescence received in the light-receiving step; and determining whether or not a fluorescence lifetime dispersion of the objects caused by amplification of the signal of the fluorescence performed in the light-receiving step or in the signal processing step is larger than a predetermined value.

Preferably, in the light-receiving step, the fluorescence is received by a photomultiplier tube and, in the signal processing step, the signal of the fluorescence received in the light-receiving step is amplified by an amplifier.

Preferably, the fluorescence measuring method further includes adjusting a gain of the photomultiplier tube or of the amplifier based on a result of determination made in the step of determining.

Preferably, the fluorescence measuring method further includes outputting a result of determination made in the determining step.

Preferably, in the outputting step, a magnitude of the fluorescence lifetime dispersion is outputted.

Preferably, in the performing signal processing step, the fluorescence lifetime is determined based on a phase difference between a modulation signal for modulating an intensity of the laser light and the signal of the fluorescence received in the light-receiving step.

Advantageous Effects of Invention

The fluorescence measuring apparatus and the fluorescence measuring method according to the present invention make it possible to determine whether accuracy of measuring fluorescence lifetime is deteriorated or not due to adjustment of the apparatus.

DESCRIPTION OF EMBODIMENTS

Hereinbelow, a flow cytometer using a fluorescence measuring apparatus and a fluorescence measuring method according to the present invention will be described with reference to the following embodiments.

First Embodiment

Figure 1:
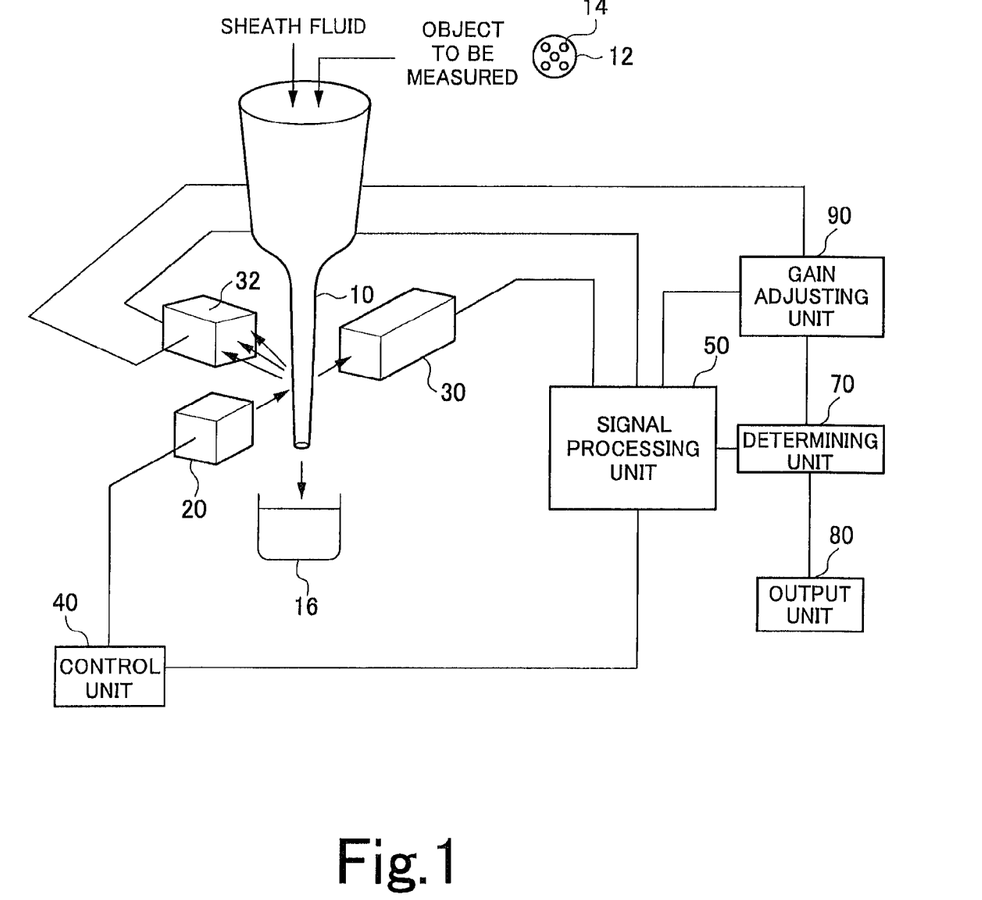
FIG. 1 is a schematic configuration diagram illustrating one example of a flow cytometer according to an embodiment of the present invention.

Configuration of Flow Cytometer
First, configuration of a flow cytometer according to an embodiment of the present invention will be described with reference to FIG. 1. FIG. 1 is a schematic configuration diagram illustrating one example of the configuration of the flow cytometer according to this embodiment. The flow cytometer can acquire information about objects to be measured by irradiating each of the objects to be measured with laser light and receiving fluorescence emitted from each of the objects to be measured irradiated with the laser light.

As illustrated in FIG. 1, the flow cytometer according to this embodiment includes a flow cell 10, a laser light source 20, a first light-receiving unit 30, a second light-receiving unit 32, a control unit 40, a signal processing unit 50, a determining unit 70, an output unit 80, and a gain adjusting unit 90. Further, a container 16 for collecting objects to be measured is provided downstream from the flow cell 10. Each of the components will be described in detail below.

Objects to be measured such as cells 12 flow inside the flow cell 10 while surrounded by a sheath fluid. As will be described later, the flow cytometer acquires information per object to be measured from fluorescence emitted when each of the objects to be measured is irradiated with laser light emitted from the laser light source 20, and therefore the cells 12 are previously labeled with a fluorochrome 14. Examples of the fluorochrome 14 used include Cyan Fluorescent Protein (CFP) and Yellow Fluorescent Protein (YFP). When flowing inside the flow cell 10, the objects to be measured are hydrodynamically focused by the surrounding sheath fluid into a narrow stream.

The laser light source 20 irradiates each of the objects to be measured with laser light whose intensity is modulated at a predetermined frequency. As the laser light source 20, for example, a semiconductor laser may be used. The output power of the laser light is, for example, 5 to 100 mW. The wavelength of the laser light is, for example, 350 to 800 nm. The intensity of the laser light emitted from the laser light source 20 is modulated using a modulation signal outputted from the control unit 40 that will be described later.

The first light-receiving unit 30 and the laser light source 20 are arranged on opposite sides of a position where the flow cell 10 is irradiated with the laser light. The first light-receiving unit 30 receives forward-scattered light emitted when each of the objects to be measured is irradiated with the laser light. The first light-receiving unit 30 has a photoelectric converter such as a photodiode. The first light-receiving unit 30 converts the received forward-scattered light into an electric signal.

The electric signal converted by the first light-receiving unit 30 is outputted to the signal processing unit 50 and used as a trigger signal that announces timing at which each of the objects to be measured passes through the position where the flow cell 10 is irradiated with the laser light.

The second light-receiving unit 32 is arranged in a direction perpendicular to both a direction, in which the laser light emitted from the laser light source 20 travels, and a direction, in which each of the objects to be measured flows inside the flow cell 10, with respect to the position where the flow cell 10 is irradiated with the laser light. The second light-receiving unit 32 receives fluorescence emitted when each of the objects to be measured is irradiated with the laser light. The second light-receiving unit 32 converts the received fluorescence into an electric signal (fluorescence signal).

Figure 2:
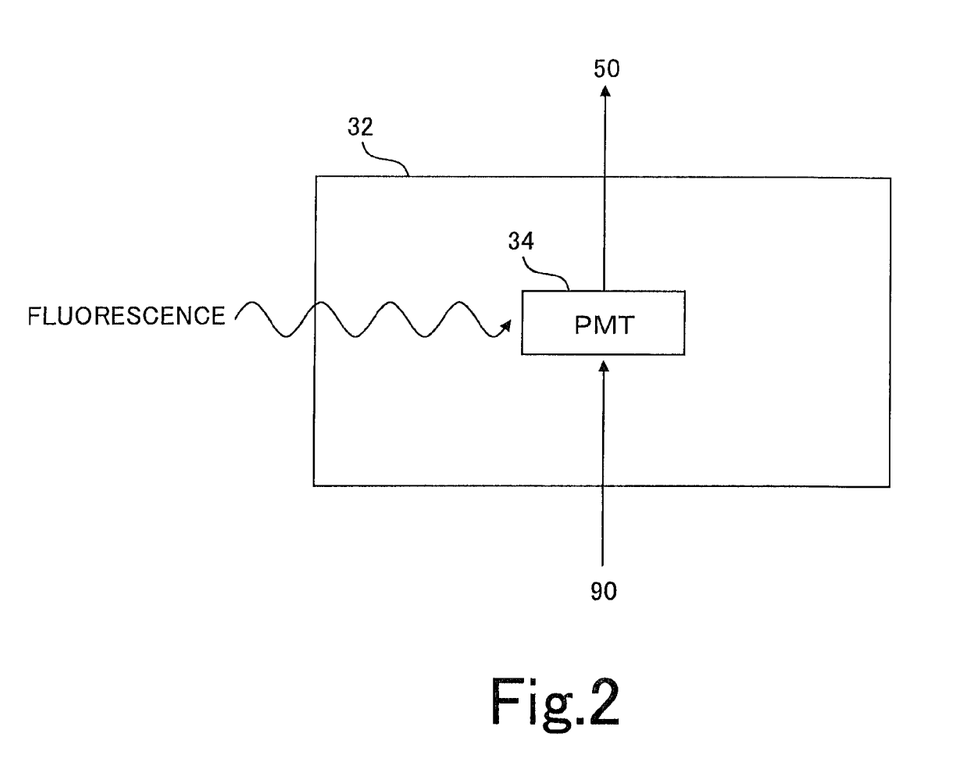
FIG. 2 is a diagram illustrating one example of a second light-receiving unit illustrated in FIG. 1.

Here, the configuration of the second light-receiving unit 32 will be described with reference to FIG. 2. FIG. 2 is a diagram illustrating one example of the second light-receiving unit 32. As illustrated in FIG. 2, the second light-receiving unit 32 has a photomultiplier tube (PMT) 34.

The electric signal converted by the photomultiplier tube 34 is outputted to the signal processing unit 50 and used as information about each object to be measured that passes through the position where the flow cell 10 is irradiated with the laser light. The gain of the photomultiplier tube 34 is adjusted by a gain adjusting unit 90.

Figure 3:
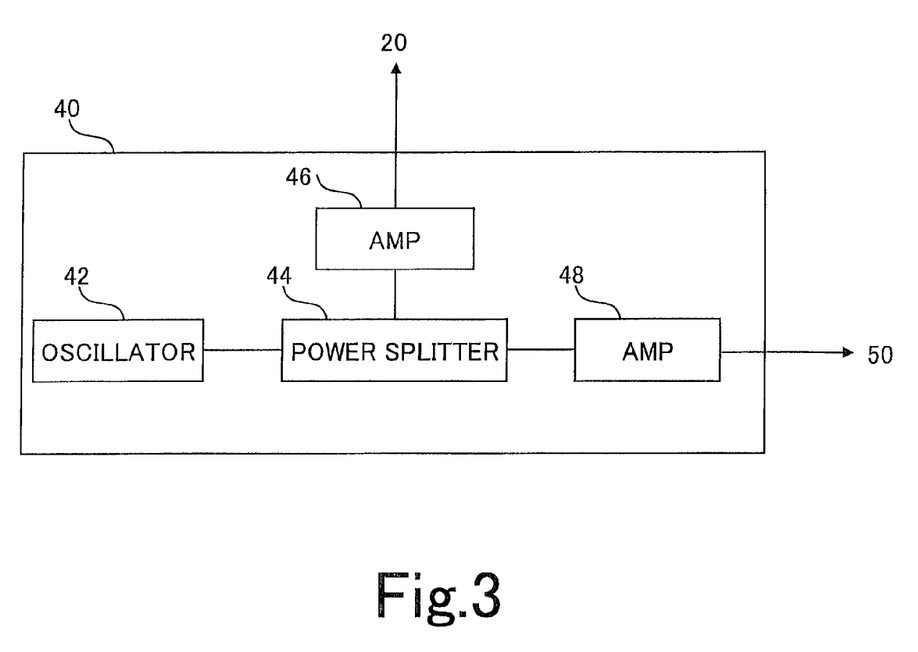
FIG. 3 is a diagram illustrating one example of a control unit illustrated in FIG. 1.

The control unit 40 will be described below. The control unit 40 controls the modulation frequency of the laser light emitted from the laser light source 20. The configuration of the control unit 40 will be described with reference to FIG. 3. FIG. 3 is a diagram illustrating one example of the control unit 40. As illustrated in FIG. 3, the control unit 40 has an oscillator 42, a power splitter 44, and amplifiers 46 and 48.

The oscillator 42 outputs a sinusoidal signal with a predetermined frequency. The sinusoidal signal outputted from the oscillator 42 is used as a modulation signal for modulating the intensity of the laser light emitted from the laser light source 20. The frequency of the sinusoidal signal is, for example, 1 to 50 MHz.

The sinusoidal signal (modulation signal) with a predetermined frequency outputted from the oscillator 42 is distributed by the power splitter 44 to the two amplifiers 46 and 48. The modulation signal amplified by the amplifier 46 is outputted to the laser light source 20. The modulation signal amplified by the amplifier 48 is outputted to the signal processing unit 50. As will be described later, the reason why the modulation signal amplified by the amplifier 48 is outputted to the signal processing unit 50 is that it is used as a reference signal to detect a signal outputted from the second light-receiving unit 32.

Figure 4:
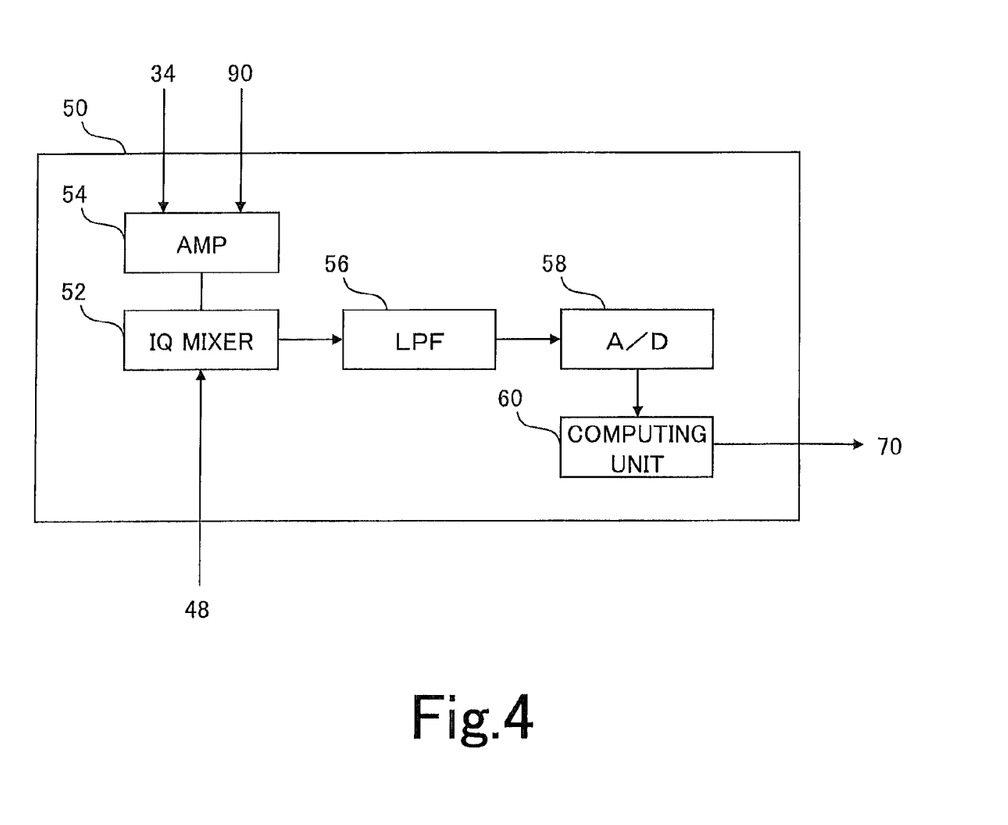
FIG. 4 is a diagram illustrating one example of a signal processing unit illustrated in FIG. 1.

The signal processing unit 50 will be described below. The signal processing unit 50 determines a fluorescence lifetime based on the phase difference between the modulation signal for modulating the intensity of the laser light and a signal of the fluorescence received by the second light-receiving unit 32 (fluorescence signal). Here, the configuration of the signal processing unit 50 will be described with reference to FIG. 4. FIG. 4 is a diagram illustrating one example of the signal processing unit 50. As illustrated in FIG. 4, the signal processing unit 50 includes an IQ mixer 52, an amplifier 54, a low-pass filter 56, an A/D converter 58, and a computing unit 60.

The IQ mixer 52 receives, as an input, the fluorescence signal outputted from the photomultiplier tube 34 of the second light-receiving unit 32 which is amplified by the amplifier 54. Further, the IQ mixer 52 receives, as an input, the reference signal outputted from the amplifier 48 of the control unit 40.

The IQ mixer 52 multiplies the fluorescence signal and the reference signal to generate a signal containing a cos component of the fluorescence signal and a high-frequency component. Further, the IQ mixer 52 multiplies the fluorescence signal and a signal obtained by shifting the phase of the reference signal by 90° to generate a signal containing a sin component of the fluorescence signal and a high-frequency component. Based on these signals, the phase difference between the modulation signal (reference signal) and the fluorescence signal can be determined.

It is to be noted that the gain of the amplifier 54 is adjusted by the gain adjusting unit 90.

The high-frequency component of the signals generated by the IQ mixer 52 is removed by the low-pass filter 56. The signals from which the high-frequency component has been removed by the low-pass filter 56 are converted by the A/D converter 58 into digital signals ($\cos \theta$, $\sin \theta$ described later). The digital signals converted by the A/D converter 58 are outputted to the computing unit 60.

The computing unit 60 determines the phase difference between the modulation signal (reference signal) and the fluorescence signal. Further, the computing unit 60 determines a fluorescence lifetime using the phase difference determined. The processing performed by the computing unit 60 will be described later in detail.

The results of computations performed by the computing unit 60 are outputted to the determining unit 70.

Referring to FIG. 1 again, the determining unit 70 will be described. The determining unit 70 determines whether or not a fluorescence lifetime dispersion of the objects caused by amplification of the fluorescence signal performed by the second light-receiving unit 32 or by the signal processing unit 50 is larger than a predetermined value. More specifically, the determining unit 70 determines whether or not the fluorescence lifetime dispersion is larger than a predetermined value due to the improper gain of the photomultiplier tube 34 or of the amplifier 54. In this way, the determining unit 70 can determine whether or not the gain of the photomultiplier tube 34 or of the amplifier 54 is proper.

Further, the determining unit 70 determines the magnitude of the fluorescence lifetime dispersion. The processing performed by the determining unit 70 will be described later in detail.

The determining unit 70 outputs the result of determination, the magnitude of the fluorescence lifetime dispersion, the fluorescence lifetime etc. to the output unit 80 and the gain adjusting unit 90.

The output unit 80 outputs the result of determination made by the determining unit 70, the magnitude of the fluorescence lifetime dispersion, and the fluorescence lifetime etc. The output unit 80 may be, for example, a display device or a printer.

The gain adjusting unit 90 adjusts the gain of the photomultiplier tube 34 or of the amplifier 54 based on the result of determination made by the determining unit 70 as to whether or not the fluorescence lifetime dispersion caused by amplification of the fluorescence signal performed by the second light-receiving unit 32 or by the signal processing unit 50 is larger than a predetermined value. The gain adjusting unit 90 may adjust either or both of the gain of the photomultiplier tube 34 and the gain of the amplifier 54. A method in which the gain adjusting unit 90 adjusts the gain of the photomultiplier tube 34 or of the amplifier 54 will be described later in detail.

The above is the schematic configuration of the flow cytometer according to this embodiment.

Signal Processing Method

Hereinbelow, the flow of signal processing performed by the signal processing unit 50 will be described.

First, a modulation signal for modulating the intensity of the laser light is outputted as a reference signal from the control unit 40 to the signal processing unit 50. The reference signal inputted into the signal processing unit 50 is, for example, a sinusoidal signal with a predetermined frequency.

Further, fluorescence emitted when each object to be measured is irradiated with the laser light is received by the second light-receiving unit 32. The second light-receiving unit 32 outputs a received fluorescence signal to the signal processing unit 50.

Then, the IQ mixer 52 multiplies the fluorescence signal and the reference signal to generate a signal containing a cos component of the fluorescence signal and a high-frequency component. Then, the high-frequency component is removed by the low-pass filter 56.

Further, the IQ mixer 52 multiplies the fluorescence signal and a signal obtained by shifting the phase of the reference signal by 90 degrees to generate a signal containing a sin component of the fluorescence signal and a high-frequency component. Then, the high-frequency component is removed by the low-pass filter 56.

Then, the computing unit 60 calculates the time average of cos component of the fluorescence signal and the time average of sin component of the fluorescence signal. The time-averaged cos and sin components of the fluorescence signal are plotted on a graph illustrated in FIG. 5. By performing the above-described signal processing on the single object to be measured, one point is plotted on the graph.

The computing unit 60 plots the time-averaged cos and sin components of the fluorescence signals derived from the individual objects to be measured (whose number is, for example, N). Further, the computing unit 60 determines the phase difference of the fluorescence signal with respect to the reference signal from a plurality of plotted points of the time-averaged cos and sin components of the fluorescence signals. For example, the computing unit 60 can determine the phase difference θ of the fluorescence signal with respect to the reference signal from the inclination of a straight line obtained by approximating a plurality of plotted points on the graph illustrated in FIG. 5 by a straight line passing through the origin.

Here, when the angular frequency of the modulation signal is represented by ω and the fluorescence lifetime of the object to be measured is represented by τ, the fluorescence lifetime τ can be determined from the phase difference θ by the following formula (1):

[Formula 1]

$$\tan\theta = \omega\tau \tag{1}$$

The computing unit 60 determines a fluorescence lifetime using the determined phase difference θ based on the above formula (1).

Determination Method

Figure 5:
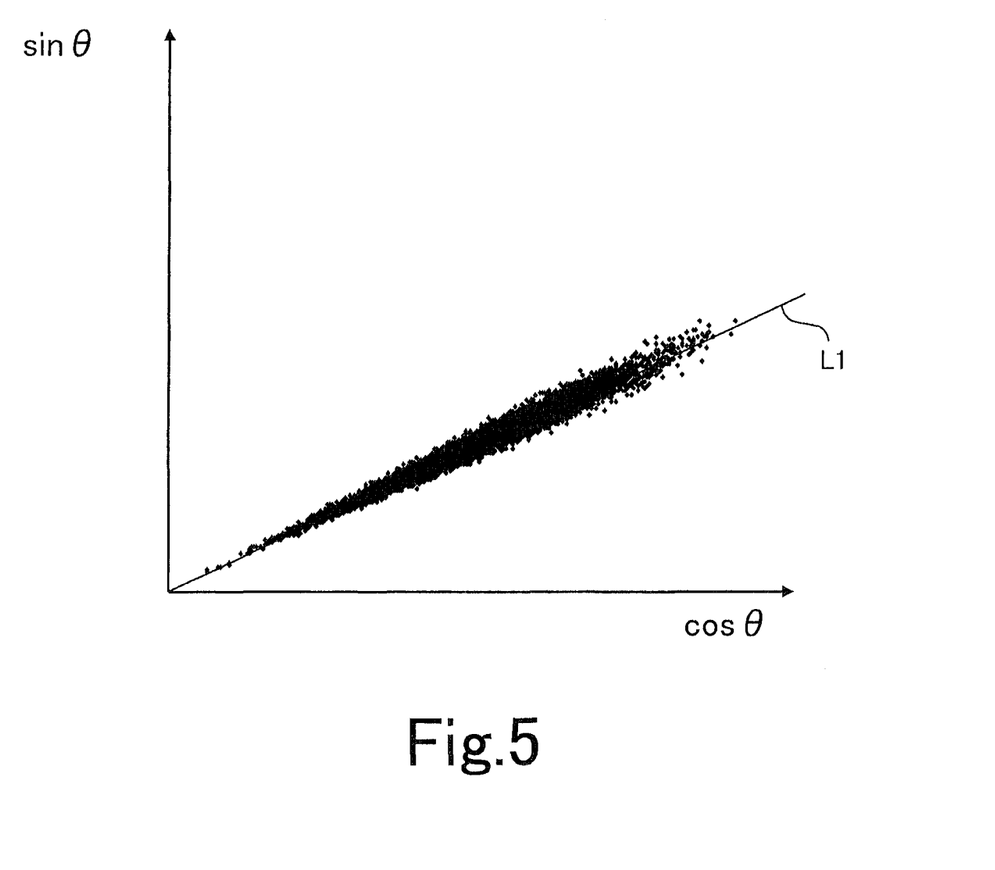
FIG. 5 is a graph illustrating one example of the phase difference of a fluorescence signal with respect to a reference signal.

Then, the determining unit 70 determines whether or not the fluorescence lifetime determined by the computing unit 60 is one determined in a state where the fluorescence lifetime dispersion caused by amplification of the fluorescence signal performed by the second light-receiving unit 32 or by the signal processing unit 50 is larger than a predetermined value. A method in which the determining unit 70 determines whether or not the fluorescence lifetime dispersion caused by amplification of the fluorescence signal performed by the second light-receiving unit 32 or by the signal processing unit 50 is larger than a predetermined value will be described below. When the gain of the photomultiplier tube 34 and the gain of the amplifier 54 are proper, as illustrated in FIG. 5, the cos and sin components of the fluorescence signals determined by the computing unit 60 are plotted along a straight line L1 passing through the origin. The straight line L1 is determined by, for example, a least squares method.

Figure 6:
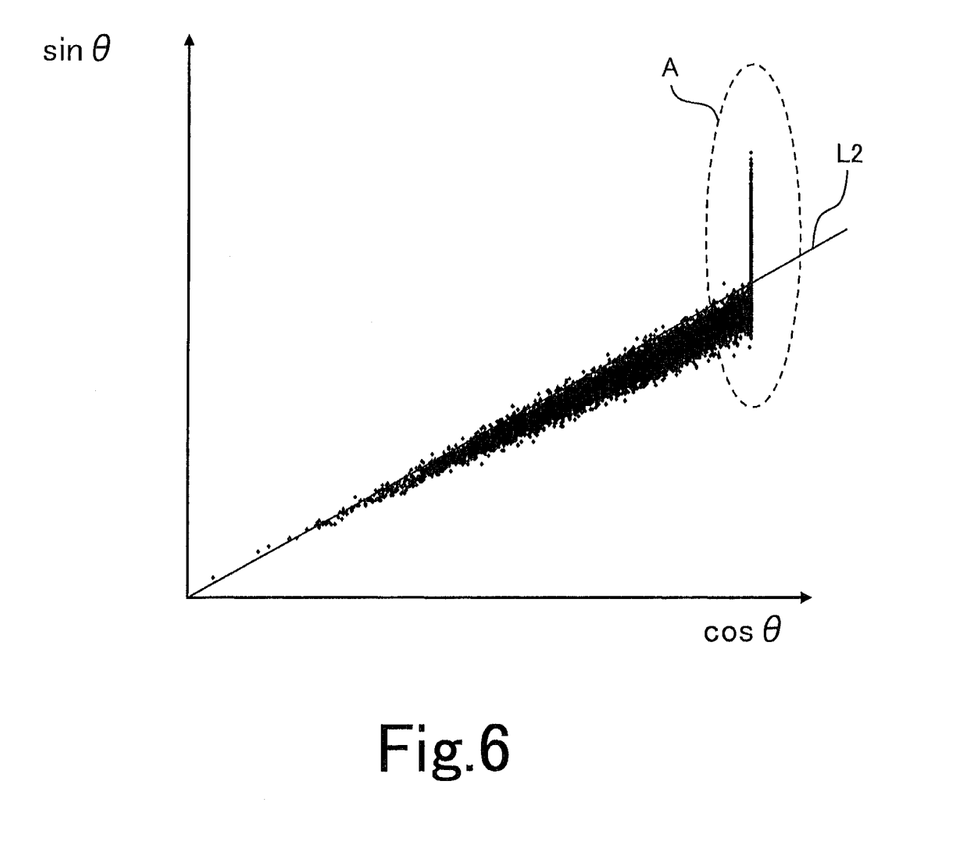
FIG. 6 is a graph illustrating one example of the phase difference of a fluorescence signal with respect to a reference signal when the gain of an amplifier is too large.

However, when the gain of the amplifier 54 is too large, the cos and sin components of the fluorescence signals determined by the computing unit 60 are plotted as illustrated in, for example, FIG. 6. In the case illustrated in FIG. 6, the time-averaged cos and sin components of the fluorescence signals plotted in a region indicated by A in FIG. 6 deviate from a straight line passing through the origin. This is because the gain of the amplifier 54 is too large and therefore the cos component of the fluorescence signal exceeds the upper limit of input range of the A/D converter 58.

As illustrated in FIG. 6, when the gain of the amplifier 54 is not proper, a straight line L2 is obtained by approximating a plurality of plotted points. In the case illustrated in FIG. 6, the cos component is saturated in the region indicated by A in FIG. 6, and therefore the inclination (tan θ) of the straight line L2 is larger than a value corresponding to the actual fluorescence lifetime. Therefore, the fluorescence lifetime τ determined based on the above formula (1) is larger than its actual value. This means that the measurement accuracy of the fluorescence lifetime τ is deteriorated.

Further, the dispersion of the plotted points around the straight line L2 in the case illustrated in FIG. 6 where the gain of the amplifier 54 is not proper is larger than the dispersion of the plotted points around the straight line L1 in the case illustrated in FIG. 5 where the gain of the amplifier 54 is proper.

Figure 7:
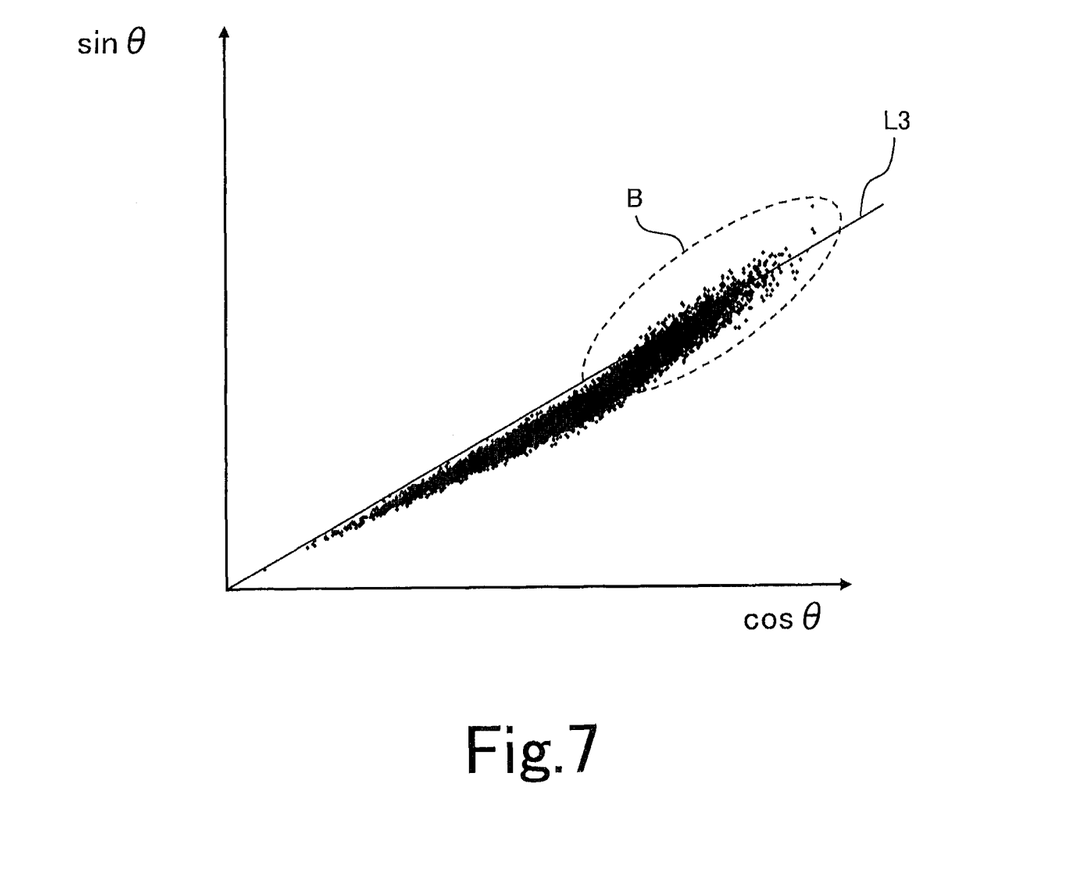
FIG. 7 is a graph illustrating one example of the phase difference of a fluorescence signal with respect to a reference signal when the gain of a photomultiplier tube is too large.

When the gain of the photomultiplier tube 34 is too large, the cos and sin components of the fluorescence signals determined by the computing unit 60 are plotted as illustrated in, for example, FIG. 7. In the case illustrated in FIG. 7, the time-averaged cos and sin components of the fluorescence signals plotted in a region indicated by B in FIG. 7 deviate from a straight line passing through the origin. This is because the gain of the photomultiplier tube 34 is too large, and therefore a saturation phenomenon occurs in the photomultiplier tube 34.

As illustrated in FIG. 7, when the gain of the photomultiplier tube 34 is not proper, a straight line L3 is obtained by approximating a plurality of plotted points. In the case illustrated in FIG. 7, a saturation phenomenon occurs in the photomultiplier tube 34 in the region indicated by B in FIG. 7, and therefore the inclination (tan θ) of the straight line L3 is larger than a value corresponding to the actual fluorescence lifetime. Therefore, the fluorescence lifetime τ determined based on the above formula (1) is larger than its actual value. This means that the measurement accuracy of the fluorescence lifetime τ is deteriorated.

Further, the dispersion of the plotted points around the straight line L3 in the case illustrated in FIG. 7 where the gain of the photomultiplier tube 34 is not proper is larger than the dispersion of the plotted points around the straight line L1 in the case illustrated in FIG. 5 where the gain of the photomultiplier tube 34 is proper.

The determining unit 70 of this embodiment determines the dispersion of the plotted points at the time when the plotted points are approximated by a straight line passing through the origin by a least squares method. Then, the determining unit 70 determines whether or not the determined fluorescence lifetime dispersion is larger than a predetermined value.

When the dispersion is larger than the predetermined value, the determining unit 70 outputs, as a determination result, a signal indicating that the fluorescence lifetime dispersion is larger than a predetermined value to the output unit 80 and the gain adjusting unit 90. On the other hand, when the dispersion is smaller than the predetermined value, the determining unit 70 outputs, as a determination result, a signal indicating that the fluorescence lifetime dispersion is smaller than a predetermined value to the output unit 80 and the gain adjusting unit 90.

Further, the determining unit 70 outputs the magnitude of the fluorescence lifetime dispersion, the fluorescence lifetime, etc. to the output unit 80 and the gain adjusting unit 90.

As described above, the fluorescence measuring apparatus according to this embodiment can determine whether or not the gain of the photomultiplier tube 34 or of the amplifier 54 is proper because the determining unit 70 determines the dispersion of a plurality of plotted points at the time when the plotted points are approximated by a straight line passing through the origin by a least squares method and determines whether or not the determined dispersion is larger than a predetermined value.

Gain Adjusting Method

Hereinbelow, a method in which the gain adjusting unit 90 adjusts the gain of the photomultiplier tube 34 or of the amplifier 54 will be described.

The gain adjusting unit 90 adjusts the gain of the photomultiplier tube 34 or of the amplifier 54 based on the determination result outputted by the determining unit 70. In this embodiment, when the signal indicating that the fluorescence lifetime dispersion is larger than a predetermined value is inputted into the gain adjusting unit 90 as the determination result, the gain adjusting unit 90 performs gain adjustment so that both the gain of the photomultiplier tube 34 and the gain of the amplifier 54 are reduced.

After the gain adjusting unit 90 adjusts the gain of the photomultiplier tube 34 and the gain of the amplifier 54, the computing unit 60 determines the phase difference θ of the fluorescence signal with respect to the reference signal from a plurality of plotted points of the time-averaged cos and sin components of the fluorescence signals derived from the individual objects to be measured (whose number is, for example, N) by the above-described signal processing method. Further, the computing unit 60 determines a fluorescence lifetime using the phase difference θ determined.

It is to be noted that when the signal indicating that the fluorescence lifetime dispersion is smaller than a predetermined value is inputted into the gain adjusting unit 90 as the determination result, the gain adjusting unit 90 keeps the gain of the photomultiplier tube 34 and the gain of the amplifier 54 as they are.

The amount of adjustment of the gain of the photomultiplier tube 34 or of the amplifier 54 is determined based on the magnitude of the fluorescence lifetime dispersion outputted from the determining unit 70. More specifically, when the magnitude of the fluorescence lifetime dispersion is larger, the amount of gain adjustment is larger.

As described above, in the fluorescence measuring apparatus according to this embodiment, the gain adjusting unit 90 adjusts the gain of the photomultiplier tube 34 and the gain of the amplifier 54 based on the magnitude of the fluorescence lifetime dispersion, and therefore the fluorescence lifetime dispersion caused by amplification of the fluorescence signal performed by the second light-receiving unit 32 or by the signal processing unit 50 can be made equal to or less than a predetermined value.

First Modified Example

In the first embodiment, as described above, the determining unit 70 determines whether or not the fluorescence lifetime dispersion, which is caused by amplification of the fluorescence signal performed by the second light-receiving unit 32 or by the signal processing unit 50, is larger than a predetermined value based on the dispersion of cos and sin components of the fluorescence signals determined by the computing unit 60 at the time when the cos and sin components of the fluorescence signals are approximated by a straight line passing through the origin. This modified example is different from the first embodiment in the method of determination made by the determining unit 70.

The determining unit 70 of this modified example determines whether or not the magnitude of a quadratic coefficient at the time when the cos and sin components of the fluorescence signals determined by the computing unit 60 are approximated by a quadratic curve passing through the origin is larger than a predetermined value.

Further, the determining unit 70 outputs the magnitude of the fluorescence lifetime dispersion (quadratic coefficient), the fluorescence lifetime, etc. to the output unit 80 and the gain adjusting unit 90.

When the gain of the photomultiplier tube 34 and the gain of the amplifier 54 are proper, as illustrated in FIG. 5, the cos and sin components of the fluorescence signals determined by the computing unit 60 are plotted along the straight line L1 passing through the origin. Therefore, the magnitude of a quadratic coefficient at the time when the cos and sin components of the fluorescence signals determined by the computing unit 60 are approximated by a quadratic curve passing through the origin is smaller than the predetermined value.

However, when the gain of the amplifier 54 is not proper as in the case illustrated in FIG. 6 or when the gain of the photomultiplier tube 34 is not proper as in the case illustrated in FIG. 7, the magnitude of a quadratic coefficient at the time when the cos and sin components of the fluorescence signals determined by the computing unit 60 are approximated by a quadratic curve passing through the origin is larger than the predetermined value.

As described above, according to this modified example, the determining unit 70 can determine whether or not the fluorescence lifetime dispersion caused by amplification of the fluorescence signal performed by the second light-receiving unit 32 or by the signal processing unit 50 is larger than a predetermined value by determining whether or not the magnitude of a quadratic coefficient at the time when the cos and sin components of the fluorescence signals determined by the computing unit 60 are approximated by a quadratic curve passing through the origin is larger than a predetermined value.

Second Modified Example

A fluorescence measuring apparatus according to this modified example is different from the first embodiment in the method of determination made by the determining unit 70.

The determining unit 70 of this modified example divides, into 5 sections, the region between the maximum value and minimum value of the cos component of the fluorescence signals determined by the computing unit 60. Further, the determining unit 70 approximates the cos and sin components of the fluorescence signals determined by the computing unit 60 by a straight line per section. Further, the determining unit 70 determines whether or not the difference in the magnitude of inclination of the approximated straight line between the sections is larger than a predetermined value. Further, when the difference in the magnitude of inclination of the approximated straight line between the sections is larger than the predetermined value, the determining unit 70 identifies the section in which the inclination of the straight line changes.

Figure 8A:
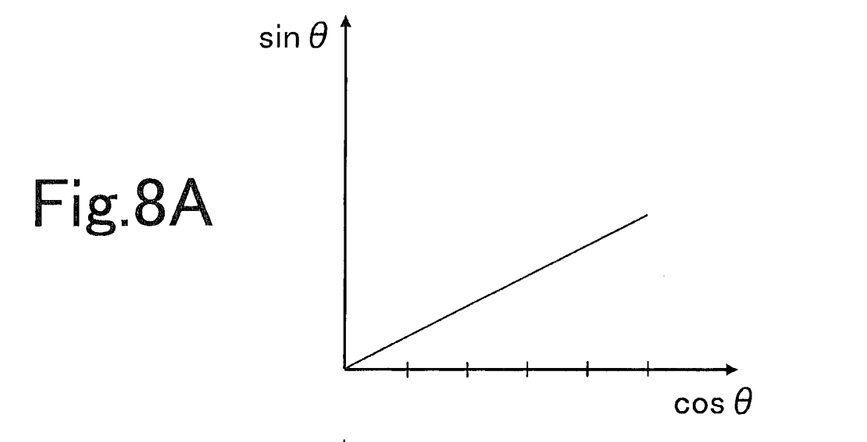
FIGS. 8A to 8C are graphs illustrating one example of the phase difference of a fluorescence signal with respect to a reference signal in Modified Example 2.

When the gain of the photomultiplier tube 34 and the gain of the amplifier 54 are proper, a straight line such as one illustrated in FIG. 8A is obtained by approximating the cos and sin components of the fluorescence signals determined by the computing unit 60 per section. The straight line illustrated in FIG. 8A is ideally the same as the straight line L1 illustrated in FIG. 5. Therefore, when the cos and sin components of the fluorescence signals determined by the computing unit 60 are approximated by a straight line per section, the difference in the magnitude of inclination of the straight line between the sections is smaller than the predetermined value.

Figure 8B:
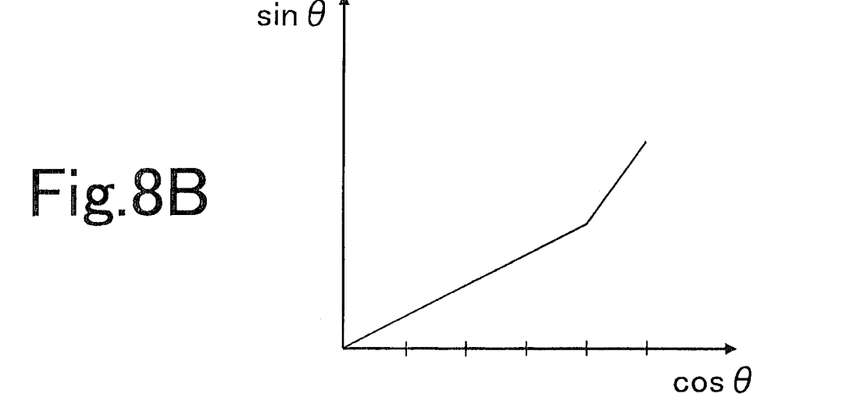

When the gain of the amplifier 54 is not proper as in the case illustrated in FIG. 6, a straight line such as one illustrated in FIG. 8B is obtained by approximating the cos and sin components of the fluorescence signals determined by the computing unit 60 per section. In FIG. 8B, for example, the difference in the magnitude of inclination of the straight line between the sections is smaller than the predetermined value within a region from the closest section to the origin up to the fourth closest section. However, the inclination of the straight line in the fifth section (i.e., in the section farthest from the origin) is significantly different from that of the straight line in the sections other than the fifth section. Therefore, the difference in the magnitude of inclination of the approximated straight line between the sections is larger than the predetermined value.

Figure 8C:
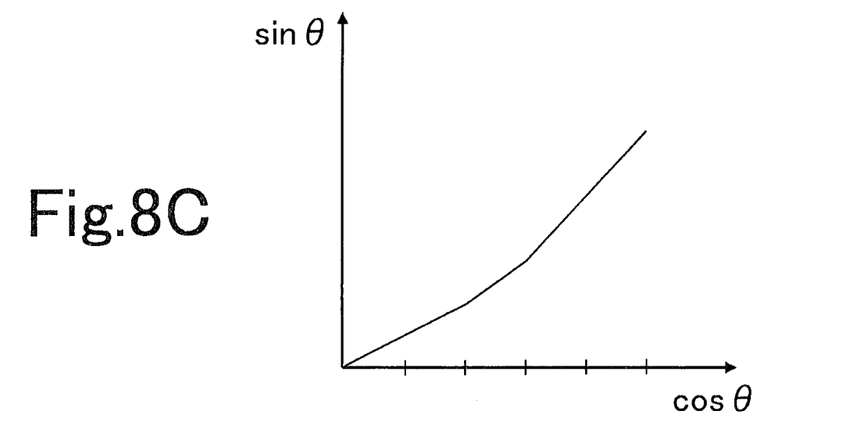

On the other hand, when the gain of the photomultiplier tube 34 is not proper as in the case illustrated in FIG. 7, a straight line such as one illustrated in FIG. 8C is obtained by approximating the cos and sin components of the fluorescence signals determined by the computing unit 60 per section. In FIG. 8C, for example, the inclination of the straight line within a region from the closest section to the origin up to the second closest section is different from that of the straight line in the fourth and fifth sections. Therefore, the difference in the magnitude of the inclination of the approximated straight line between the sections is larger than the predetermined value.

The determining unit 70 of this modified example identifies the section in which the inclination of the straight line changes, and therefore can differentiate between when the gain of the amplifier 54 is not proper as in the case illustrated in FIG. 6 and when the gain of the photomultiplier tube 34 is not proper as in the case illustrated in FIG. 7. Therefore, when the gain of the photomultiplier tube 34 or of the amplifier 54 is not proper, the determining unit 70 of this modified example outputs a signal indicating which of the gain of the photomultiplier tube 34 and the gain of the amplifier 54 is not proper to the output unit 80 and the gain adjusting unit 90.

The gain adjusting unit 90 of this modified example performs gain adjustment based on the result of determination made by the determining unit 70 so that either of the gain of the photomultiplier tube 34 and the gain of the amplifier 54 is reduced.

As described above, according to this modified example, the determining unit 70 can determine which of the second light-receiving unit 32 and the signal processing unit 50 causes the fluorescence lifetime dispersion larger than a predetermined value by approximating the cos and sin components of the fluorescence signals determined by the computing unit 60 by a straight line per section among a plurality of sections.

It is to be noted that in this modified example, the region between the maximum value and minimum value of the cos component of the fluorescence signals is divided into five sections, but the number of sections is not limited thereto.

Second Embodiment

In the case of the flow cytometer according to the above-described embodiment or modified example, the gain of the photomultiplier tube 34 or of the amplifier 54 can be adjusted by the gain adjusting unit 90 when it is not proper. However, when the flow cytometer is used by a skilled user, there is a case where the adjustment of gain of the photomultiplier tube 34 or of the amplifier 54 is preferably performed by the user himself or herself. Therefore, a flow cytometer according to a second embodiment of the present invention is intended to prevent a user from overlooking the fact that the gain of the photomultiplier tube 34 or of the amplifier 54 is not proper based on the premise that the gain of the photomultiplier tube 34 or of the amplifier 54 is adjusted by the user himself or herself.

Figure 9:
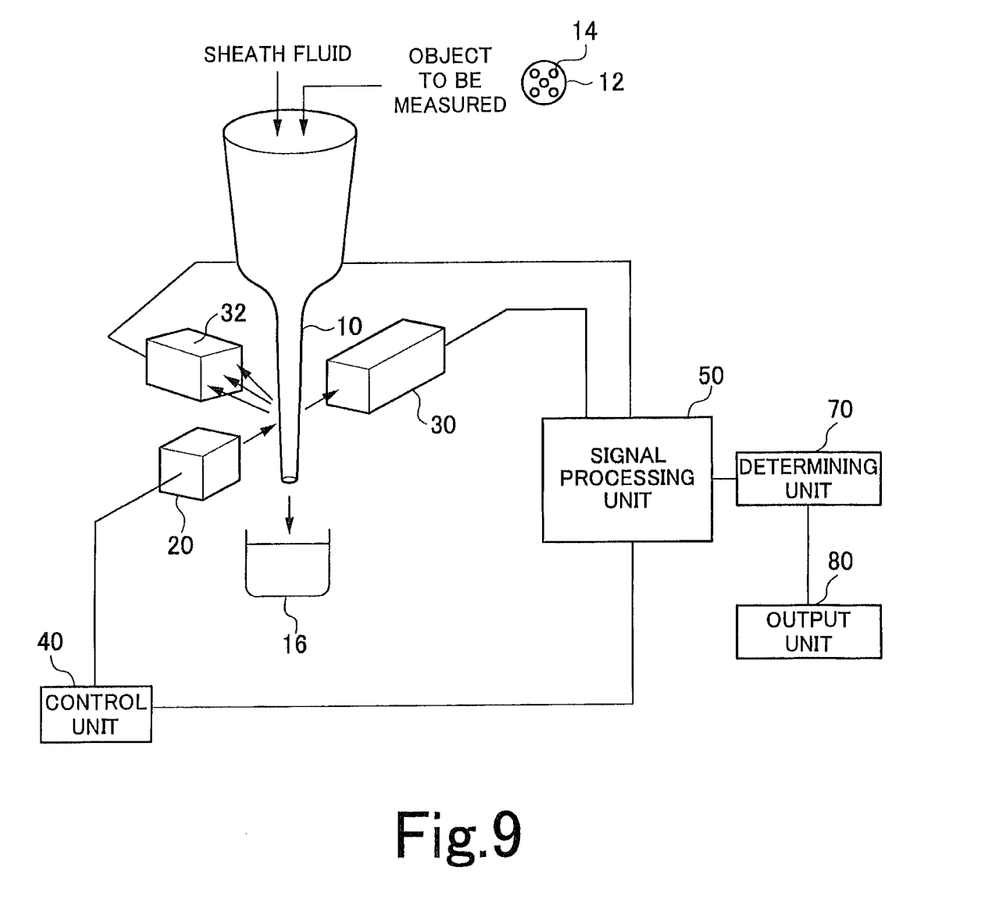
FIG. 9 is a schematic configuration diagram illustrating one example of a flow cytometer according to another embodiment of the present invention.

Here, the configuration of the flow cytometer according to the second embodiment will be described with reference to FIG. 9. FIG. 9 is a schematic configuration diagram illustrating one example of the configuration of the flow cytometer according to this embodiment. The basic configuration of the flow cytometer according to this embodiment is the same as that of the above-described first embodiment. Therefore, the description of the same components as the first embodiment will not be repeated and a difference in configuration between the first and second embodiments will be described below.

As illustrated in FIG. 9, the flow cytometer according to this embodiment includes a flow cell 10, a laser light source 20, a first light-receiving unit 30, a second light-receiving unit 32, a control unit 40, a signal processing unit 50, a determining unit 70, and an output unit 80. The flow cytometer according to this embodiment is the same as the first embodiment except that it does not include a gain adjusting unit.

The gain of a photomultiplier tube 34 of the second light-receiving unit 32 is adjusted by a user. The gain of an amplifier 54 is also adjusted by the user.

The determining unit 70 outputs the result of determination, the magnitude of the fluorescence lifetime dispersion, the fluorescence lifetime etc. to the output unit 80.

Further, the output unit 80 outputs the result of determination made by the determining unit 70, the magnitude of the fluorescence lifetime dispersion, and the fluorescence lifetime etc.

In this embodiment, the result of determination made by the determining unit 70, the magnitude of the fluorescence lifetime dispersion, and the fluorescence lifetime etc. are outputted by the output unit 80, and therefore it is possible, when the gain of the photomultiplier tube 34 or of the amplifier 54 is not proper, to prevent the user from overlooking it.

Although the fluorescence measuring apparatus and the fluorescence measuring method according to the present invention have been described above in detail, the present invention is not limited to the above embodiments and modified examples. Further, it is apparent that various modifications and changes may be made without departing from the scope of the present invention.

REFERENCE SIGNS LIST 10 flow cell
12 cell
14 fluorochrome
16 container
20 laser light source
30 first light-receiving unit
32 second light-receiving unit
34 photomultiplier tube
40 control unit
42 oscillator
44 power splitter
46, 48 amplifier
50 signal processing unit
52 IQ mixer
54 amplifier
56 low-pass filter
58 A/D converter
60 computing unit
70 determining unit
80 output unit
90 gain adjusting unit

The invention claimed is:

1. A fluorescence measuring apparatus for measuring fluorescence emitted when objects to be measured are irradiated with laser light, comprising:
   a laser light source configured to irradiate each of the objects to be measured with intensity-modulated laser light;
   an oscillator configured to output a modulation signal to modulate an intensity of the laser light irradiated from the laser light source;
   a light receiver configured to receive fluorescence emitted when each of the objects to be measured is irradiated with the laser light and that outputs fluorescence signals corresponding to the objects respectively;
   a signal processor configured to multiply each fluorescence signal and the modulation signal to generate a signal containing an in-phase component of the fluorescence signal and to multiply the fluorescence signal and a signal obtained by shifting a phase of the modulation signal by 90 degrees to generate a signal containing a quadrature component of the fluorescence signal to determine a fluorescence lifetime using the in-phase and quadrature components; and a determiner configured to group the fluorescence signals into a number of sections by values of the in-phase components, identify relations between the in-phase and quadrature components by linear regression lines in the sections respectively, and determine whether or not a difference of slopes of the linear regression lines is larger than a predetermined value.

2. The fluorescence measuring apparatus according to claim 1, wherein the light receiver has a photomultiplier tube, the signal processor has an amplifier that amplifies the signal of the fluorescence received by the light receiver, and the determiner is further configured to identify the section in which the slope of the linear regression line changes and indicates which of a gain of the photomultiplier tube and a gain of the amplifier is not proper.

3. The fluorescence measuring apparatus according to claim 2, further comprising a gain adjuster configured to adjust a gain of the photomultiplier tube or of the amplifier based on a result of determination made by the determiner.

4. The fluorescence measuring apparatus according to claim 1, further comprising an output configured to output a result of determination made by the determiner.

5. The fluorescence measuring apparatus according to claim 4, wherein the determiner determines whether or not a dispersion of the fluorescence lifetime is larger than a predetermined value, and the output is configured to output a magnitude of the dispersion.

6. The fluorescence measuring apparatus according to claim 1, wherein the determiner is further configured to determine which of a gain of the light receiver and a gain of the signal processor is not proper based on the differences of slopes of the linear regression lines.

7. A fluorescence measuring method for measuring fluorescence emitted when objects to be measured are irradiated with laser light, the method comprising:

outputting a modulation signal for modulating an intensity of laser light irradiated from a laser light source;

irradiating each of the objects to be measured with intensity-modulated laser light emitted from the laser light source;

receiving fluorescence emitted when each of the objects to be measured is irradiated with the laser light;

outputting fluorescence signals corresponding to the objects respectively;

multiplying each fluorescence signal and the modulation signal to generate a signal containing a in-phase component of the fluorescence signal;

multiplying each fluorescence signal and a signal obtained by shifting a phase of the modulation signal by 90 degrees to generate a signal containing a quadrature component of the fluorescence signal to determines a fluorescence lifetime using the in-phase and quadrature components;

grouping the fluorescence signals into a number of sections by values of the in-phase components;

identifying relations between the in-phase and quadrature components by linear regression lines in the sections respectively; and determining whether or not a difference of slopes of the linear regression lines is larger than a predetermined value.

8. The fluorescence measuring method according to claim 7, wherein, the fluorescence is received by a photomultiplier tube and the fluorescence signal is output by the photomultiplier, the fluorescence signal is amplified by an amplifier, and the method further comprising identifying the section in which the slope of the linear regression line changes and indicating which of a pin of the photomultiplier tube and a gain of the amplifier is not proper.

9. The fluorescence measuring method according to claim 8, further comprising adjusting a gain of the photomultiplier tube or of the amplifier based on a result of determination made in the step of determining.

10. The fluorescence measuring method according to claim 7, further comprising outputting a result of determination made in the determining step.

11. The fluorescence measuring method according to claim 10, further comprising determining whether or not a dispersion of the fluorescence lifetime is larger than a predetermined value, and outputting a magnitude of the dispersion.

12. The fluorescence measuring method according to claim 7, further comprising determining which of a gain of a light receiver and a gain of a signal processor is not proper based on the differences of slopes of the linear regression lines.

* * * * *